United States Patent [19]

Grobman

[11] 4,453,086
[45] Jun. 5, 1984

[54] ELECTRON BEAM SYSTEM WITH REDUCED CHARGE BUILDUP

[75] Inventor: Warren D. Grobman, Yorktown Heights, N.Y.

[73] Assignee: International Business Machines Corporation, Armonk, N.Y.

[21] Appl. No.: 336,465

[22] Filed: Dec. 31, 1981

[51] Int. Cl.$^3$ .............................................. C08J 7/10
[52] U.S. Cl. .................................. 250/307; 250/492.3
[58] Field of Search .................. 250/307, 492.3, 492.1

[56] References Cited

U.S. PATENT DOCUMENTS

| | | | |
|---|---|---|---|
| 2,064,369 | 12/1936 | Biggs | 313/636 |
| 3,376,469 | 4/1968 | Consoli | 315/111.81 |
| 3,507,709 | 4/1970 | Bower | 148/1.5 |
| 4,022,927 | 5/1977 | Pfeiffer et al. | 430/5 |
| 4,041,300 | 8/1977 | Blount | 362/13 |
| 4,076,558 | 2/1978 | Rupprecht et al. | 148/1.5 |
| 4,152,601 | 5/1979 | Kadota et al. | 378/35 |

OTHER PUBLICATIONS

Grobman, W. D., and Koch, E. E., "Photoemission from Organic Molecular Crystals." In: Ley, L. and Cardona, M., *Photoemission in Solids II*, (Topics in Applied Physics), vol. 27, Berlin, Heidelberg, N.Y., Springer-Verlag, 1979, pp. 261-263.

Primary Examiner—Janice A. Howell
Assistant Examiner—Constantine Hannaher
Attorney, Agent, or Firm—Jackson E. Stanland

[57] ABSTRACT

In electron beam testing systems wherein high energy, high resolution electron beams are used to test lithographic masks, a technique and apparatus are described for discharging electrons which are left on the surface of the mask, and which alter the input trajectory of the electron beam. The materials used in these masks are such that induced photoconductivity and photoemissivity are extremely low and are incapable of providing sufficient electron discharge. A thin, low work function coating is applied over the entire mask surface, the coating being transparent to the radiation which will later be incident upon the mask when it is used in a fabrication process. Due to induced photoemission in the thin coating layer, enough photoemitted electrons will be produced to balance the buildup of electrons from the electron beam, thereby discharging the surface of the mask. The electron beam is a high energy beam, having energies greater than about 5000 eV, and a resolution less than about 1 micrometer.

27 Claims, 2 Drawing Figures

ELECTRON BEAM SYSTEM WITH REDUCED CHARGE BUILDUP

DESCRIPTION

1. Technical Field

This invention relates to a method and apparatus for reducing charge buildup on objects being scanned at high resolution and consequently, high beam energy, in electron beam systems, and especially in such systems where excess electrons cannot be easily removed by conventional techniques.

2. Background Art

The use of electron beams is known for many purposes, including the testing of masks. For example, X-ray masks and other lithographic masks, such as chrome-on-glass masks, can be tested before use by the application of a scanning electron beam to the mask. Typically, these masks are comprised of a conductive material on an insulating substrate. An example is an X-ray mask comprising an X-ray opaque material such as gold, on an X-ray transparent substrate, such as a thin film of silicon or a nitride. Another mask which is often used in optical lithography is one in which a patterned layer of chromium is formed on a glass substrate.

When these masks are tested by the use of an electron beam, an input electron beam is directed to a particular location on the mask, and the back-scattered electrons are collected and observed. The number of back-scattered electrons is a measure of the presence or absence of the opaque pattern at a particular point on the substrate. For example, a "clear" defect is a defect where the opaque masking material is absent in a location where it should be present in accordance with the data pattern used to produce the mask. An "opaque" defect is one where the masking material is present at a location where it shouldn't be in accordance with the data pattern used to produce the mask.

During testing, there is often a buildup of electron charge on the surface of the mask, due to the high energy incoming electron beam. The buildup of negative charge on the mask alters the accuracy of this test procedure, since the incoming beam often follows the wrong trajectory due to the repelling force of the electrons on the surface of the mask. Thus, it is important to prevent this negative charge buildup during the testing procedure.

Numerous techniques exist in the prior art for preventing charge buildup. For example, thin gold coatings have been placed on the mask in order to conduct away the electronic charge. However, these coatings have to be removed before the mask can be used in order to obtain maximum contrast for the mask. This is an additional step, and leads to the possibility that the mask may be damaged during removal of the conductive layer.

Another technique for preventing electron charge buildup is to lower the electron beam voltage until secondary emission from the mask surface exactly counteracts electron beam absorption, so that charging does not occur. However, this approach compromises the resolution of the testing procedure and is not a suitable technique for testing high density mask patterns.

Still another technique for preventing charge buildup uses the photoconductive effect, wherein the material is exposed to a light beam. This produces many carriers for the discharge of the material. For example, induced photoconductivity is used to remove charge from the surface of a photocopier drum, in those copiers which use organic photoconductors. However, induced photoconductivity cannot be used to discharge a mask comprising a patterned conductive layer. In particular, for masks such as chrome-on-glass masks, sufficiently large induced photoconductivity in glass is very hard to achieve.

The photoconductivity effect works best for the discharge of charge buildup in materials such as organic polymers and in cases where only very small rates of charging are involved, which is contrary to the case in electron beam inspection systems (where electron beams of energy greater than about 5000 eV, and with a resolution less than about 1 micrometer, are used). To be effective, the induced photoconductivity must produce a large number of hole-electron pairs having high mobilities. These carriers must also be able to travel long distances without recombining. In X-ray masks and masks such as chrome-on-glass, the photoconductivity effect is ineffective to provide discharge, because the mobility of carriers in these materials is low. Thus, it can be predicted that the use of this effect to provide carrier discharge in masks using a conductive material on quartz or glass, etc. is ineffective, especially in the important case of large inspection beam current (which is typical in high resolution electron beam inspection systems).

Another technique for discharging a charged surface is to apply an additional charged beam, such as an ion beam or a low energy electron beam. A positive ion beam would counteract the buildup of negative charges due to the testing electron beam, while the second electron beam of low energy would cause counteracting positive charging due to excessive emission of secondary electrons. Both of these approaches requires additional equipment, are complex and expensive, and involve currents smaller than those required to prevent charging in inspection systems.

The text *Photoemission in Solids II*, edited by Ley and Cardony (Springer-Verlag, Berlin, Heidelberg, New York, 1979) contains a chapter (5) describing photoemission from organic molecular crystals. In section 5.1.1 "Charging Effects", pp. 262–263, the authors describe results of photoemission on organic solids. These materials are very poor conductors and undergo charging effects which tend to smear the energy spectrum of the photoemitted electrons. In order to provide a sharper spectrum of emitted electrons, the charging effect on the surface of the organic solid is reduced in a variety of ways. One of these ways is the use of an electron beam flood of the organic material surface for the creation of electrons to balance the positive charge due to the photoemission.

Materials such as those used in X-ray masks and other masks do not easily lend themselves to the above-mentioned conventional approaches for relieving charge buildup. If a thin conductive layer is used to carry away the excess charge carriers, this layer will have to be removed before use of the mask, since the transparency of the mask to the radiation to be used in processing will be adversely affected. Still further, the materials used in these masks do not yield the required number of carriers by photoemission or photoconductivity when low energy excitation is provided. It is significantly preferable to use low energy processes, as the use of high energy processes would require the use of expensive lamps, windows, etc.

In the analysis of masks and other such devices, it is often important that the transparency of the mask to the radiation intended for use with it be maintained. Therefore, conventionally used coatings would in many cases have to be removed prior to mask use, since they could be opaque to that radiation. For example, a coating placed on a chrome-on-glass mask in order to enhance induced photoconductivity could be opaque to the types of radiation that are later used with the mask in the fabrication of circuits, etc. This coating would have to be removed, which is an additional step that creates the possibility of mask damage.

Another detriment to the use of coatings is that these coatings often have to be thick enough to provide the desired effect, i.e., the production of sufficient amounts of compensating charge carriers. However, coatings of that thickness would adversely affect the contrast and aspect ratio obtained with the masks and therefore have to be removed for this reason, also.

Accordingly, it is a primary object of this invention to provide a technique for preventing excess electron charge buildup on masks of the type used in lithographic processes, when tested with electron beams of high energy (i.e., greater than approximately 5000 eV) and high resolution (i.e., less than approximately 1 micrometer).

It is another object of this invention to provide a technique and apparatus for the prevention of electron charge buildup during electron beam testing of structures comprising a conductive layer opaque to the electron beam radiation on an insulating layer.

It is another object of this invention to provide a technique for compensating electron charge buildup on masks which are tested by electron beam radiation, wherein additional coatings do not have to be removed prior to utilization of the mask in a lithography process.

It is a further object of this invention to provide a technique for compensating electron charge buildup on the surface of devices comprising an opaque conductive or nonconductive layer on an insulating layer, where sufficient numbers of compensating charge particles can easily be produced.

It is a still further object of this invention to provide an apparatus and technique for the removal of excess electron charges on lithographic masks subjected to electron beam testing, which is inexpensive and uses low energy processes.

It is another object of this invention to provide discharge of mask surfaces during electron beam testing by a simple technique that does not alter the contrast or aspect ratio of the masks.

It is another object of this invention to provide a technique and means for removal of excess electron charges on the surface of a lithographic mask being subjected to electron beam testing, where the mask is fabricated of materials in which the effect of induced photoconductivity cannot be readily used to provide a sufficient amount of compensating charge particles.

SUMMARY OF THE INVENTION

A technique and apparatus for providing discharge of electrons on the surface of a conductive material are provided, wherein conventional techniques cannot be used to provide discharge. In particular, this technique is advantageously applied to the electron beam testing of lithography masks, where the masks are comprised of a patterned layer on an insulating substrate, where the photoconductive effect and photoemissive effect cannot be used to provide sufficient discharge of electrons left by a high resolution testing electron beam having energies greater than about 5000 eV.

The lithographic mask to be tested is coated with a thin layer of a material having a low work function $\phi$ and is illuminated by a low energy ultraviolet light simultaneously with the application of the testing electron beam. The low work function coating is transparent to the electron beam and to the radiation which will later be used in lithographic fabrication processes. Therefore, the coating need not be removed after testing, in contrast with the coatings of the prior art which had to be removed.

The coating is chosen to have a low work function so that photoemission of electrons easily occurs. The positive charge due to the photoemission of electrons balances against the negative charge buildup due to the electrons in the testing electron beam. An example of a suitable coating is a cesium telluride (CsTe) coating which can be used on a chromium-on-glass mask. Typically the coating is sufficiently thin that the properties of the mask are not affected during its later use, and is sufficiently thick that it is free of pinholes. Suitable thicknesses are approximately 200–1000 Å for the coating layer.

These and other objects, features, and advantages will be apparent from the following more particular description of the preferred embodiments.

BEST MODE FOR CARRYING OUT THE INVENTION

Figure 1:
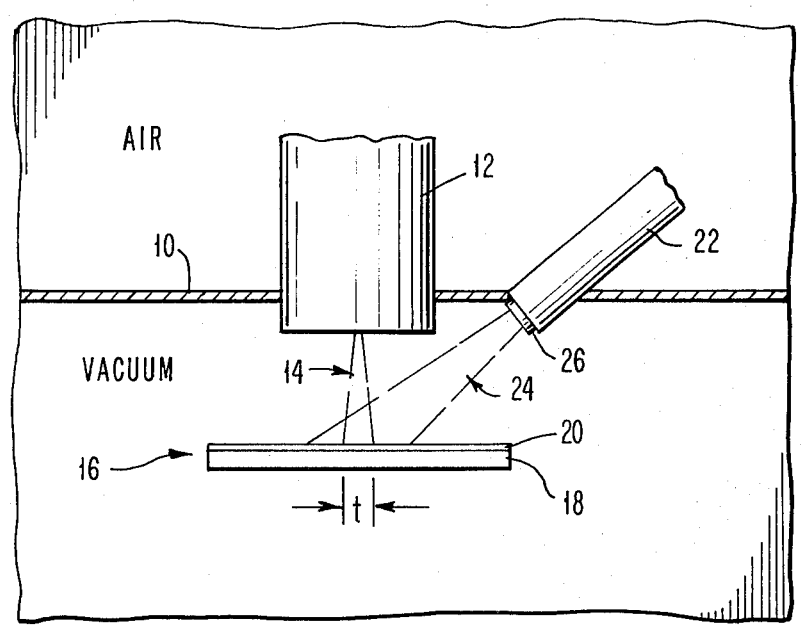
FIG. 1 is a schematic diagram of an apparatus suitable to provide discharge of electrons on the surface of a lithography mask being tested by an electron beam.

An electron beam test apparatus for testing lithography masks is shown in FIG. 1. The apparatus is comprised of a vacuum chamber 10 for producing a vacuum therein by known means. An electron beam 12 is used to produce an input beam of electrons 14 having energies at least about 5000 eV, and a resolution less than about 1 micrometer in width, which impinges upon the mask plate 16. The mask plate is comprised of the actual lithography mask 18 and a thin coating 20 of a low work function photoemissive material, such as CsTe. The scanning field of the electron beam 14 is indicated by the dimension t.

A standard source 22 of ultraviolet wavelength, such as a hydrogen or mercury discharge lamp, produces a light beam 24 which impinges on the photoemissive coating over an area which includes the electron beam scan field t. As an example, the width of the beam 24 on coating 20 can be approximately 1 cm, which is sufficient to easily overlap the scanning field t (which is typically a few millimeters wide).

Electron beam 14 is used to test the mask in the manner previously described. The ultraviolet beam 24 produces free electrons by the photoemissive effect, and thereby creates a net positive charge on coating 20. This counteracts the buildup of electrons from electron beam 14, and discharges the coating surface so that the trajectory of the incoming electron beam is not adversely altered.

Figure 2:
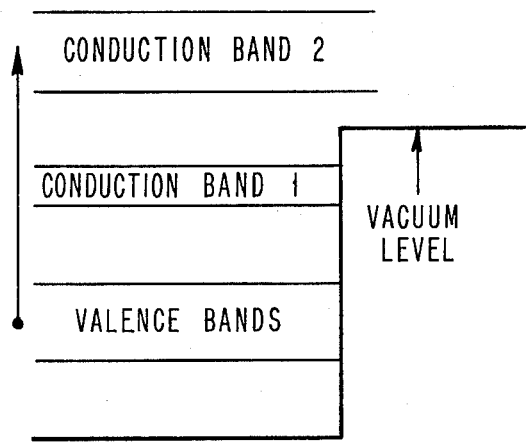
FIG. 2 is an energy band diagram of the coating on the lithography mask of FIG. 1, indicating the production of electrons therein by the photoemission effect.

FIG. 2 is an energy band diagram of the coating 20 located on mask 18. The incoming ultraviolet radiation has an energy $h\nu_2$, which is sufficient to overcome the work function of the photoemissive material 20, and move electrons into the conduction band 2, which is above the vacuum level. Therefore, electrons will be released from the surface of coating 20, creating a positive charge thereon which offsets the buildup of electrons from the beam 14.

In this technique, the ultraviolet radiation produced by lamp 22 is of low energy, typically less than 6 eV. This means that the window 26 through which the ultraviolet radiation passes into the vacuum chamber 10 can be made from a conventional material, such as quartz.

In one example, a mask 18 was comprised of a patterned chromium layer on glass, and the coating 20 was CsTe of a thickness 200–1000 Å. The ultraviolet light beam contained photons having a peak energy of 5 eV, which was sufficient to raise electrons in coating 20 above the work function, which is approximately 1–2 eV. A coating 20 of this thickness does not have to be removed after electron beam testing, since it will be transparent to the radiation used with a chromium-on-glass mask. In this technique for preventing negative charge buildup on the mask plate 16, a surface effect is utilized. For example, even though glass is not easily discharged when it contains surface electrons, it is not the primary material to consider. The buildup and discharge of electrons occurs on the CsTe layer, so the presence of the glass has essentially no effect.

In this technique, the current due to the photoemission in coating 20 is sufficiently great that it will balance the rate at which free electrons are produced on the surface of coating 20. That is, the number of electrons produced by photoemission equals the number of electrons arriving from electron beam 14. This photoemission current is a function of the work function of coating 20, for a given energy in the beam 24.

Although CsTe has been mentioned as a coating material, other materials can be used. These materials are chosen to have a low work function so that large numbers of free electrons can be produced by the photoemission effect, without requiring high energy ultraviolet radiation. Further, the nature of the coating is such that only a thin layer need be used, and the coating must be of a material which can be left on the mask after the electron beam testing. Since the coating 20 can be thin, the aspect ratio of the mask will not be seriously altered by its presence, and it will be transparent to the radiation which is later incident on the mask during a lithographic fabrication process. The coating is necessary because of the nature of the materials being tested. These materials are not highly photoemissive or photoconductive, and are not easily discharged of excess electrons by any other technique. Other examples for the coating 20 are the following: CsI, and other materials commonly used for cathodes in photocells, such as other alkali metal halides.

In the practice of this invention, high energy electron beam testing of lithographic masks (such as optical and X-ray masks) is now possible without the adverse results of electron charge buildup. In particular, the invention is applicable to those situations where the mask cannot be used with a coating that later has to be removed, and also where the mask contains materials which don't exhibit strong photoconductive or photoemissive effects. A thin photoemissive coating of a sufficiently low work function material will enable the production of enough secondary electrons when flooded by low energy ultraviolet light to balance the large number of electrons left on the surface by the test electron beam. The term "low work function" means that the material will yield a sufficiently large rate of positive charging when hit by an ultraviolet beam from a standard source having energies <6 eV, to balance the net negative charge being deposited by a potentially high current inspection electron beam.

While the invention has been described in terms of preferred embodiments thereof, it will be understood by those of skill in the art that other variations can be made which will not depart from the spirit and scope of the present invention.

Having thus described my invention, what I claim as new, and desire to secure by Letters Patent is:

1. A method for testing a mask to be used in a lithographic process wherein radiation is directed onto said mask, said mask including a patterned layer of material on a substrate in which photoconductivity and photoemissivity cannot be easily induced, including the steps of:

coating said patterned layer with a thin layer of a low work function material in which photoemission can readily be induced, said coating being substantially transparent to an electron beam and to said radiation, scanning said patterned layer with an electron beam to test for defects in said patterned layer, said electron beam causing a buildup of electrons on the surface of said coated mask, and directing ultraviolet light onto said coated mask in an area overlapping the area of said mask being hit by said electron beam to cause photoemission of electrons from said thin coating layer in an amount to produce a positive charge thereon sufficient to balance the negative charge induced by the incidence of electrons from said electron beam.

2. The method of claim 1, where said electron beam has a high beam energy greater than about 5000 eV.

3. The method of claim 1, where said mask is an X-ray mask.

4. The method of claim 1, where said mask is an optical mask.

5. The method of claim 4, where said optical mask is a Cr on glass mask.

6. The method of claim 1, where the thickness of said thin coating layer is less than approximately 1000 Å.

7. The method of claim 1, where said mask substrate is an insulating material.

8. The method of claim 1, where said thin coating layer has a work function less than approximately 2 eV.

9. The method of claim 1, where said ultraviolet radiation includes a spectrum of energies less than approximately 6 eV.

10. The method of claim 1, where said thin coating layer is chosen from the group consisting of CsTe, CsI, and alkali metal halides.

11. The method of claim 1, where said mask is a Cr on glass mask, and said thin coating layer has a thickness less than about 1000 Å and a work function less than about 3 eV.

12. A method for testing lithographic masks to be used in lithographic processes wherein radiation is directed onto said mask, including the steps of:

placing said masks in a vacuum environment in which a scanning electron beam will be directed to said mask for detection of said faults therein, said mask including a substrate having a patterned layer thereon, said patterned layer including first regions which are transparent to said radiation and second regions which are opaque to said radiation, said substrate being comprised of a material in which photoconductivity and photoemission are only very weakly induced by ultraviolet excitation having an energy spectrum less than about 6 eV, coating said mask with a thin layer of a material having a low work function in which photoemission can readily be induced, said coating being substantially transparent to said radiation, testing said mask by impinging a high resolution scanning electron beam thereon over an area termed a scan field, said testing producing a net negative charge due to the electrons incident on said mask, producing a net positive charge of an amount sufficient to balance the said negative charge in order to discharge said mask, said net positive charge being produced by the application of ultraviolet energy having an energy spectrum of energies less than 6 eV, where said ultraviolet radiation is applied to said thin coating layer over an area which overlaps said scan field of said electron beam.

13. The method of claim 12, where said scan field of said electron beam is a few millimeters wide.

14. The method of claim 12, where said mask is comprised of a patterned conductive layer on an insulating substrate.

15. The method of claim 12, where said thin coating layer has a thickness less than about 1000 Å.

16. The method of claim 15, where said thin coating layer has a work function less than about 3 eV.

17. The method of claim 16, where said thin coating layer is chosen from the group consisting of CsTe, CsI, and alkali metal halides.

18. The method of claim 16, where said mask is an optical lithography mask.

19. The method of claim 16, where said mask is an X-ray lithography mask.

20. The method of claim 12, where said mask is comprised of a patterned layer of Cr on a glass substrate, and said thin coating layer has a thickness less than about 1000 Å.

21. An apparatus for testing for lithography masks, said mask being used in lithographic processes wherein radiation is directed onto said masks for exposure of layers behind said mask, comprising in combination:

a mask comprising a patterned layer located on a substrate, said patterned layer including first regions which are substantially transparent to said radiation and second regions which are substantially opaque to said radiation, said substrate being comprised of a material which does not strongly support induced photoconductivity and photoemission at excitations less than about 6 eV, a thin coating layer formed on said patterned layer comprised of a material which exhibits a strong photoemissive effect at an excitation less than about 6 eV, said coating layer being sufficiently thin that it is transparent to said radiation, a vacuum chamber into which said mask is placed for testing, an electron beam source for directing a high energy scanning beam of electrons into said vacuum chamber and onto said coated mask for testing said mask, said electron beam striking said mask over an area defined as a scan field, the intensity of said electron beam being sufficient that negative charge will occur on said coated mask of an amount sufficient to alter the trajectory of said electron beam to thereby cause errors in the testing of said mask, means for shining ultraviolet light of an energy less than about 6 eV on said mask in an area overlapping said scanned field for producing photoemission from said thin coating layer of an amount to produce a net positive charge which balances the net negative charge produced by said electron beam to thereby sufficiently discharge the surface of said coated mask so that the trajectory of the scanning electron beam is not adversely affected.

22. The apparatus of claim 21, where said mask is a Cr on glass mask.

23. The apparatus of claim 21, where said mask is an X-ray mask comprising a patterned layer of a heavy metal on a substrate.

24. The apparatus of claim 21, where said thin coating layer has a work function less than approximately 3 eV.

25. The apparatus of claim 21, where said thin coating layer has a thickness less than about 1000 Å.

26. The apparatus of claim 21, where said electron beam has a beam energy greater than about 5000 eV.

27. The apparatus of claim 21, where said electron beam has a resolution less than about 1 micrometer.

* * * * *